(12) United States Patent
Russe

(10) Patent No.: US 10,617,556 B2
(45) Date of Patent: Apr. 14, 2020

(54) STIMULATORY FLUID COLLECTION DEVICE

(71) Applicant: Rupa Russe, Durham, NC (US)

(72) Inventor: Rupa Russe, Durham, NC (US)

( * ) Notice: Subject to any disclaimer, the term of this patent is extended or adjusted under 35 U.S.C. 154(b) by 60 days.

(21) Appl. No.: 16/017,938

(22) Filed: Jun. 25, 2018

(65) Prior Publication Data

US 2019/0388264 A1   Dec. 26, 2019

(51) Int. Cl.
*A61F 5/455* (2006.01)
*A61H 19/00* (2006.01)

(52) U.S. Cl.
CPC .......... *A61F 5/4553* (2013.01); *A61H 19/32* (2013.01); *A61H 19/50* (2013.01)

(58) Field of Classification Search
CPC .............. A61F 5/4553; A61F 13/2045; A61F 5/44–4556; A61H 19/40–50; A61H 19/00–50; A61H 21/00
See application file for complete search history.

(56) References Cited

U.S. PATENT DOCUMENTS

| 3,404,682 | A | | 10/1968 | Waldron | |
|---|---|---|---|---|---|
| 3,841,333 | A | * | 10/1974 | Zalucki | A61F 5/4553 604/330 |
| 5,295,984 | A | * | 3/1994 | Contente | A61K 9/0036 604/317 |
| 2008/0077097 | A1 | * | 3/2008 | Chambers | A61F 5/4553 604/330 |
| 2018/0028350 | A1 | * | 2/2018 | Wilson | A61F 5/4553 |
| 2018/0140458 | A1 | * | 5/2018 | Brockway | A61F 5/4553 |
| 2018/0214298 | A1 | * | 8/2018 | Medas | A61F 5/4553 |
| 2019/0224039 | A1 | * | 7/2019 | Garriga I Rodo | A61F 5/4404 |
| 2019/0314191 | A1 | * | 10/2019 | Bobarikin | A61F 5/4553 |

* cited by examiner

*Primary Examiner* — Thaddeus B Cox
(74) *Attorney, Agent, or Firm* — NCCU School of Law–IP Clinic; Mark E. Atkinson; Dana Sisk

(57) ABSTRACT

A stimulating collection cup collects female bodily fluids and provides stimulation for the penis of a user's partner. The stimulating collection cup is easy to use and has an open end with a rim, an elongated body, an inner and outer wall, holes for airway access, texture for stimulating the penis of a user's partner, and a pulling stem for easy removal. The stem also includes protrusions for stimulation.

10 Claims, 5 Drawing Sheets

STIMULATORY FLUID COLLECTION DEVICE

FIELD OF THE INVENTION

The present invention relates to a stimulatory bodily fluid collection device. More particularly, the invention pertains to a menstrual cup that provides stimulation to the male penis during intercourse.

BACKGROUND OF THE INVENTION

The following description is not an admission that any of the information provided herein is prior art or relevant to the present invention, or that any publication specifically or implicitly referenced is prior art. Any publications cited in this description are incorporated by reference herein. Where a definition or use of a term in an incorporated reference is inconsistent or contrary to the definition of that term provided herein, the definition of that term provided herein applies and the definition of that term in the reference does not apply.

Currently, most menstrual cups only allow for the capture of female bodily fluids. These menstrual cups, however, are not designed to sexually stimulate a penis during intercourse. A woman is less likely to become pregnant during her menstrual cycle. Thus, encouraging sexual activity during the phase of a woman's menstrual cycle is valuable as it supports intimacy and lessens the likelihood of unwanted pregnancy. Current devices are specifically designed to act only as a collection cup.

Additionally, most menstrual cups include pull tabs that are blunt and rigid making intercourse uncomfortable for a male. Furthermore, while the exterior of current menstrual cups may provide a removal tab, the tab itself does not provide stimulation for the male penis upon contact.

Furthermore, stimulating products such as toys or condoms are costly for consumers. And as mentioned above current menstrual cups are not user friendly and do not encourage intercourse or any stimulation of the male penis during a female menstruation.

For the foregoing reasons, there is a need for a stimulating collection cup that provides both a stimulator for the male penis and a bodily fluid collector for a female during menstruation.

SUMMARY OF THE INVENTION

The present invention is directed to a stimulatory fluid collection device which is used as a collector of female bodily fluids during the menstrual cycle and a stimulator for the male penis. The device comprises an elongated body with an open top end and closed bottom end, with an inner wall surface that is configured as a reservoir for collection of bodily fluids. In one embodiment, the inner wall is smooth. The collection device has an upper rim and a stem, located on the closed bottom end, which also serves as a pull tab. In an embodiment of the invention, the device is a menstrual cup. In another embodiment of the present invention, the exterior of the collection device acts as a stimulator for the male penis during intercourse. In certain embodiments, the outer wall surface comprises a texture that includes one or more grooves, raised ridges, raised bumps or a combination thereof regularly distributed on the outer wall surface, covering entire outer wall surface or approximately 40% to 70% of the outer wall surface. Alternatively, the outer wall of the stimulating collection device comprises one or more grooves, raised ridges, raised bumps or any combination thereof in irregularly distributed, covering entire outer wall surface or approximately 40% to 70% of the outer wall surface. In another embodiment, the outer wall of the stimulating collection device comprises one or more grooves, raised ridges, raised bumps or any combination thereof in irregularly or regularly distributed, covering about 90% of the outer wall surface.

An embodiment of the invention provides a stem that is used for removal of the device that is also configured to stimulate the male penis. A further embodiment of the invention comprises a stem comprising a plurality of protrusions used to stimulate the penis of the user's partner.

In one embodiment, the stimulatory fluid collection device comprises an elongated body comprising a wall having an open top end, a closed bottom end, an inner wall surface defining a collection reservoir configured for collecting and retaining bodily fluid, an outer wall surface, and a plurality of perforations. In one exemplary embodiment, the outer wall surface comprises texture. The top end of the wall comprises an upper rim section, and the bottom end of the wall comprises a stem.

In yet another embodiment, the stimulatory fluid collection device comprises a conical shape. In one embodiment, the stimulatory fluid collection device further comprises an elastomeric material. In a further embodiment, the elastomeric material is silicon rubber.

In still another embodiment, the plurality of perforations is evenly spaced and extend from an inner end at the inner wall surface to an outer end at the outer wall surface to permit air passage between the inner wall surface and the outer wall surface.

In one embodiment, the stem facilitates insertion and removal of device from a user's vagina.

In yet another embodiment, the stem is configured to stimulate the penis of the user's partner.

In still another embodiment, the stem comprises a plurality of protrusions and the plurality of protrusion are configured to stimulate the penis of the user's partner.

In another embodiment, the stem comprises a single protrusion comprising texture to stimulate the penis of a user's partner.

In yet another embodiment, texture comprises one or more grooves, ridges, raised bumps or any combination thereof and evenly spaced on the outer wall surface.

In a further embodiment, the texture comprises one or more grooves, raised ridges, raised bumps or any combination thereof, covering about 40% to about 70% of the outer wall surface.

In another embodiment, the texture is regularly distributed on the outer wall surface. In yet another embodiment, the texture is irregularly distributed on the outer wall surface.

In another embodiment, the device is compressed during insertion and is resilient for restoring to the cup's original shape after being inserted into a user's vagina.

In one embodiment, a conical shaped stimulatory fluid collection device comprises an elongated body that includes a silicon rubber wall having an open top end, a closed bottom end, an inner wall surface defining a collection reservoir configured for collecting and retaining bodily fluid, an outer wall surface, and a plurality of perforations.

In one exemplary embodiment, the outer wall surface comprises texture.

In another embodiment, the perforations are evenly spaced and extend from an inner end at the inner wall surface to an outer end at the outer wall surface to permit air passage between the inner wall surface and the outer wall surface.

In yet another embodiment, the top end of the wall comprises an upper rim section. In one embodiment, each perforation is located adjacent to upper rim section.

In still another embodiment, the bottom end of the wall comprises a stem, wherein the stem, located on the closed bottom end, comprises a single protrusion. In an embodiment, the single protrusion comprises the texture that is configured to stimulate the penis of a user's partner. In one embodiment, the texture on the single protrusion comprises a plurality of raised grooves.

In yet another embodiment, the outer wall surface of the conical shaped device comprises grooves, raised ridges, raised bumps or any combination thereof.

In another embodiment, a stimulatory fluid collection device comprises an elongated body comprising a silicon rubber wall having an open top end, a closed bottom end, an inner wall surface defining a collection reservoir configured for collecting and retaining bodily fluid, an outer wall surface, and a plurality of perforations.

In one embodiment, the outer wall surface comprises texture and the top end of the wall comprises an upper rim section. In yet another embodiment, the bottom end of the wall comprises a stem, and the stem comprises a plurality of protrusions that facilitate removal of the device from the vagina of a user. In a further embodiment, protrusions are configured to stimulate the penis of a user's partner.

In yet another embodiment, the stem comprises a texture and is configured to stimulate a male penis.

In yet another embodiment, texture comprises one or more grooves, ridges, raised bumps or any combination thereof and the texture is regularly distributed on the outer wall surface.

In yet another embodiment, the texture is irregularly distributed on the outer wall surface.

Various objects, features, aspects and advantages of the inventive subject matter will become more apparent from the following detailed description of exemplary embodiments, along with the accompanying figures in which like numerals represent like components.

DETAILED DESCRIPTION

A stimulating collection device for a user is designed and manufactured to collect and retain bodily fluids within an inner reservoir, and to stimulate the penis of a user's partner during sexual activity.

Furthermore, as used herein, and unless the context dictates otherwise, the term "user" is intended to include any human with a vagina. The term "holes" and "perforation" are used interchangeably in the description herein. The terms "stimulatory fluid collection device", "collection device" and "device" are used interchangeably in the description herein.

As used in the description herein and throughout the claims that follow, the meaning of "a," "an," and "the" includes plural reference unless the context clearly dictates otherwise. Also, as used in the description herein, the meaning of "in" includes "into" and "on" unless the context clearly dictates otherwise.

As used herein, the term "about" in conjunction with a numeral refers to a range of that numeral starting from 10% below the absolute of the numeral to 10% above the absolute of the numeral, inclusive.

Figure 1:
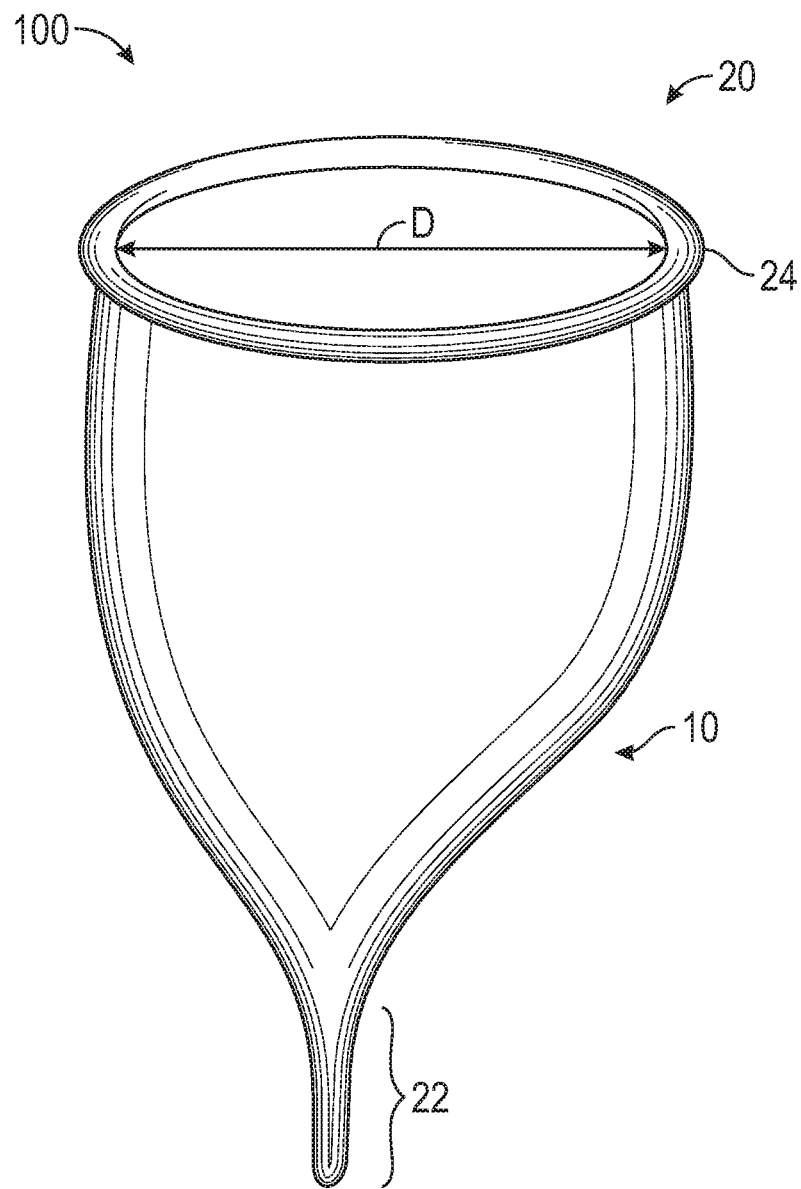
FIG. 1 is an exemplary configuration of an angled side view of a stimulatory fluid collection device.
Figure 2:
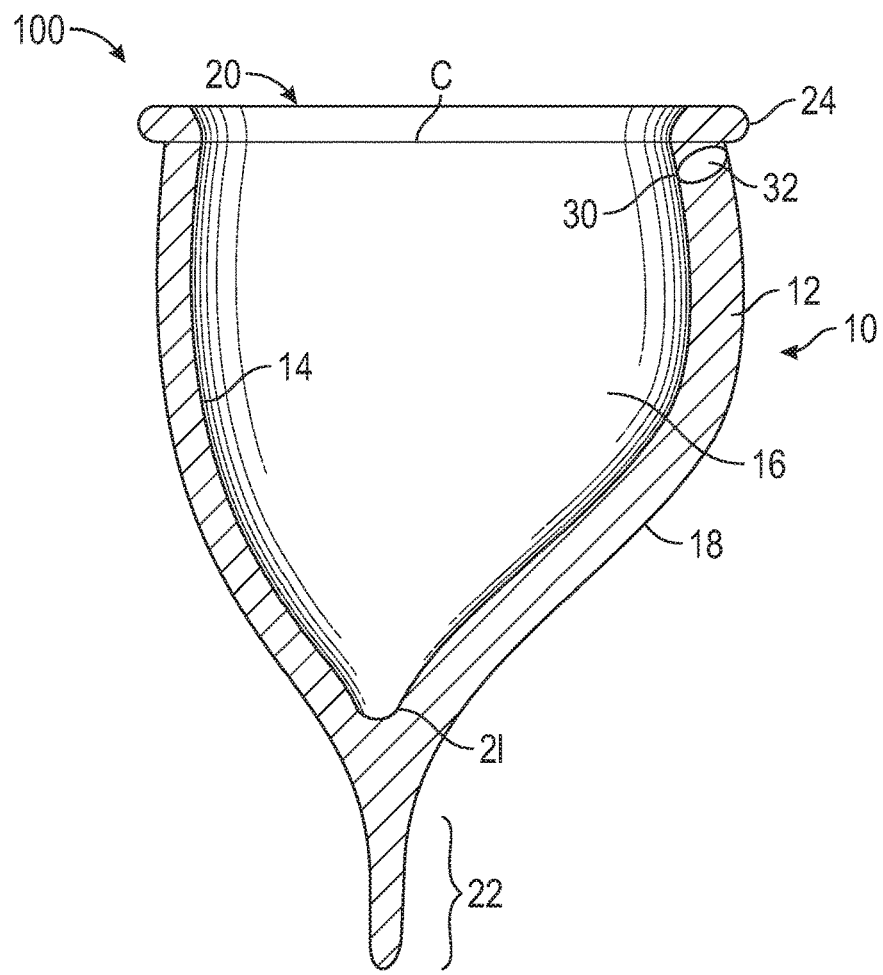
FIG. 2 is an exemplary configuration of a cross-section of a stimulatory fluid collection device.

Exemplary configurations are schematically depicted in FIGS. 1 and 2, in which stimulatory fluid collection device 100 configured to be used in a vagina (not shown) comprises an elongated body 10 comprising wall 12, inner wall surface 14 that defines collection reservoir 16 adapted for collection and retention of bodily fluids, and outer wall surface 18. In an embodiment, elongated body 10 extends from open top end 20 that includes upper rim section 24, to closed bottom end 21. In one embodiment, top end 20 includes a predetermined diameter D (see FIG. 1). In one embodiment, D is about 3 cm to about 5 cm. In another embodiment, D is about 4 cm to about 5 cm. And in an alternative embodiment, D is about 4.4 cm.

In one embodiment, upper rim section 24 is designed to strengthen open top end 20 to prevent device 100 from collapsing while in vagina (not shown). In an exemplary embodiment, upper rim section 24 is rounded at open top end 20 to provide the strength to hold device 100 in place. In another exemplary embodiment, circumference C under upper rim section 24 is about 10 cm to about 15 cm (see FIG. 2). In one exemplary embodiment, C is about 12 cm. And in an alternative embodiment, C is about 14.3 cm. In an exemplary embodiment, the thickness of wall 12, i.e., the distance between the inner wall surface 14 and outer wall surface 18, is about 3 mm to 4.5 mm. A skilled person in the art will appreciate other thickness for upper rim section 24 and wall 12. In an exemplary embodiment, device 100 is configured to retain from about 13 mL to about 16 mL of liquid in reservoir 16.

In an exemplary embodiment, elongated body 10 is conical. A skilled person in the art will be readily able to select an alternative shape for the device based on the operating conditions and requirements in the configurations contemplated herein.

In one embodiment, the material of construction for collection device 100 comprises a flexible elastomeric material such as silicone rubber or other similar material that are resilient and durable that can withstand heat used for sanitizing device 100. The flexibility of the elastomeric material facilitates device 100 to return to its original shape after device 100 is compressed for insertion into a user's vagina (not shown).

Figure 5:
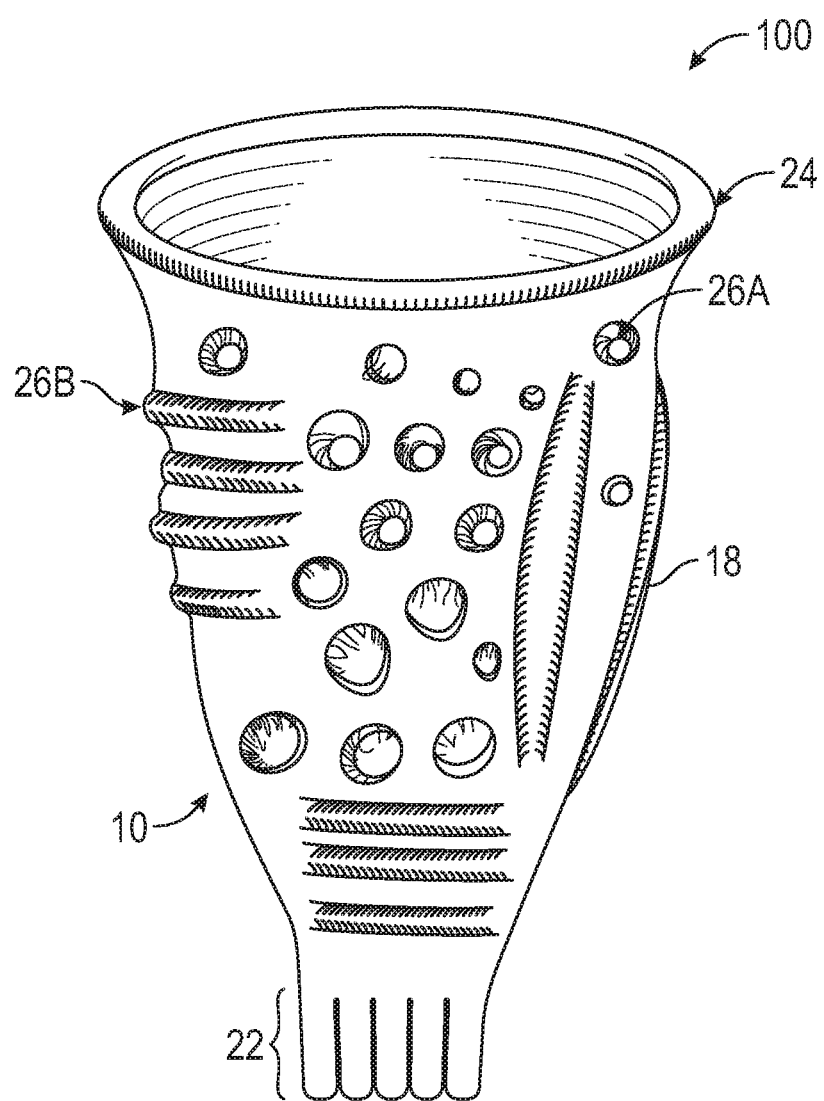
FIG. 5 is an exemplary embodiment of a front angled view of a stimulatory fluid collection device comprising a plurality of protrusions with raised ridges and raised bumps on the body of the device.

In an exemplary embodiment, the bottom end of the outer wall surface 18 of stimulatory fluid collection device 100 comprises stem 22. In an embodiment, stem 22 facilitates insertion and removal of device 100 from a user's vagina. In another embodiment, stem 22 terminates at closed bottom end 21 and comprises a single protrusion (as shown in FIG. 1). Alternatively, stem 22 comprises a plurality of protrusions which are designed to stimulate the penis of a user's partner (as shown in FIG. 5). An exemplary embodiment as depicted in FIG. 5 also illustrates outer wall 18 with raised bumps 26A and raised ridges 26B that assist in stimulating a penis of a user's partner. In an embodiment, each protrusion is about 2 mm to about 10 mm in length. In an alternative embodiment, each protrusion is flexible to provide comfort to the user while she is inserting device 100.

In an exemplary embodiment, collection device 100 is formed in an injection mold and stem 22, wall 12 and each protrusion are integrally joined and comprise the same material, i.e., an elastomeric material such as silicon.

Figure 3:
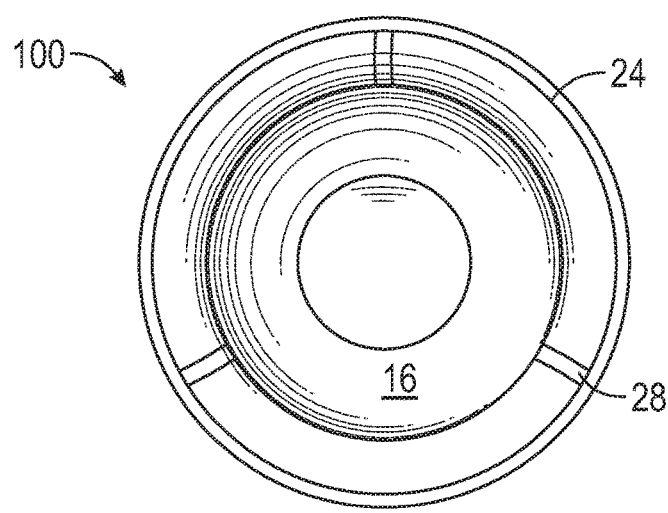
FIG. 3 is an exemplary configuration of a top view of a stimulatory fluid collection device.

As shown in FIGS. 2 and 3, stimulatory collection device 100 comprises a plurality of evenly spaced perforations 28, wherein each perforation 28 extends from inner end 30 located at inner wall surface 14 to an outer end 32 located at outer wall surface 18. In one embodiment, each perforation is located adjacent to upper rim section 24 (see FIG. 2). In another embodiment, each perforation 28 is about 1.4 mm to about 3.2 mm below upper rim section 24. In an embodiment, perforations 28 permit air passage between inner wall surface 14 and outer wall surface 18, as device 100 is inserted and removed from the user's vagina, to achieve air pressure equilibrium inside collection reservoir 16. In one exemplary embodiment, perforations 28 are about 0.1 mm to about 0.7 mm in diameter. In another embodiment, each perforation 28 is about 0.5 mm.

Figure 6:
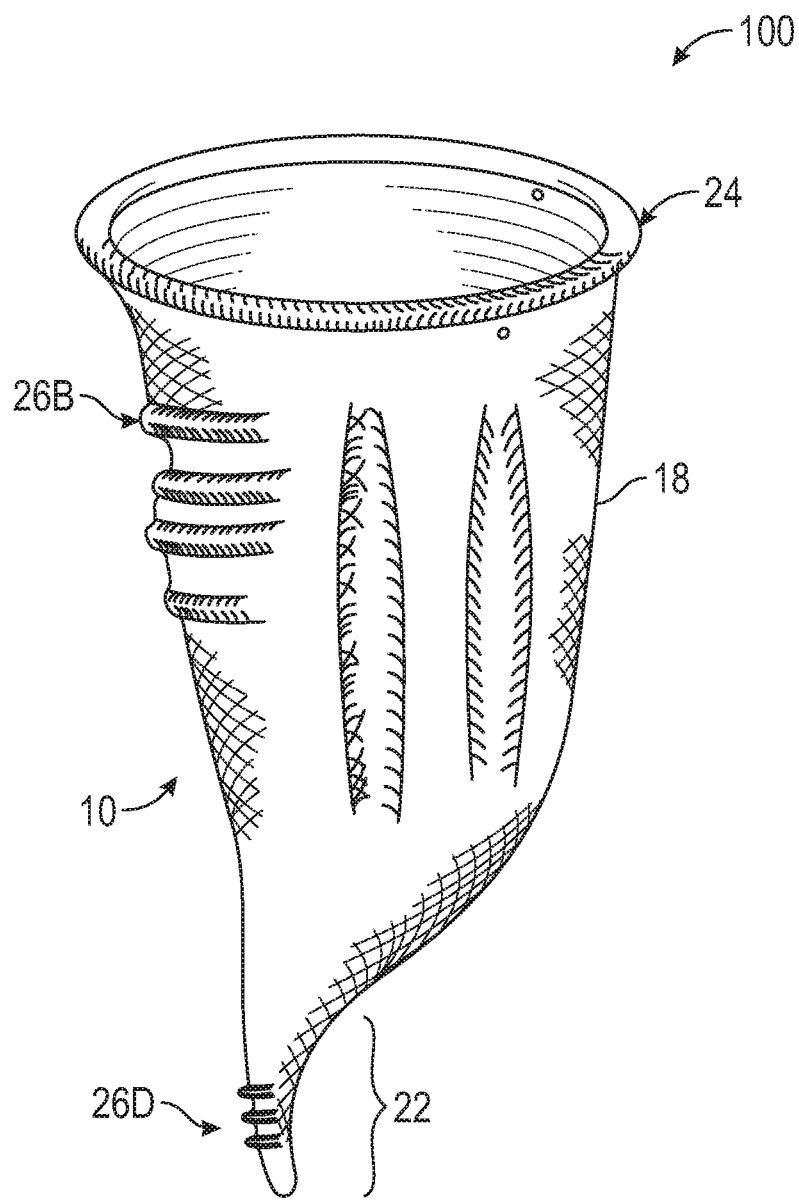
FIG. 6 is an exemplary embodiment of a side angled view of a stimulatory fluid collection device comprising raised ridges on the stem, and irregularly distributed grooves and raised ridges on the body of the device.

In an exemplary embodiment, outer wall surface 18 comprises texture 26A, 26B, 26C, 26D designed to provide stimulation to the penis of a user's partner (as depicted in FIGS. 5 and 6). FIGS. 4A, 4B, 4C and 4D are exemplary embodiments of texture configured for stimulation purposes. In one embodiment, texture comprises one or more grooves, raised ridges, raised bumps or any combination thereof on outer wall 18.

Figure 4A:
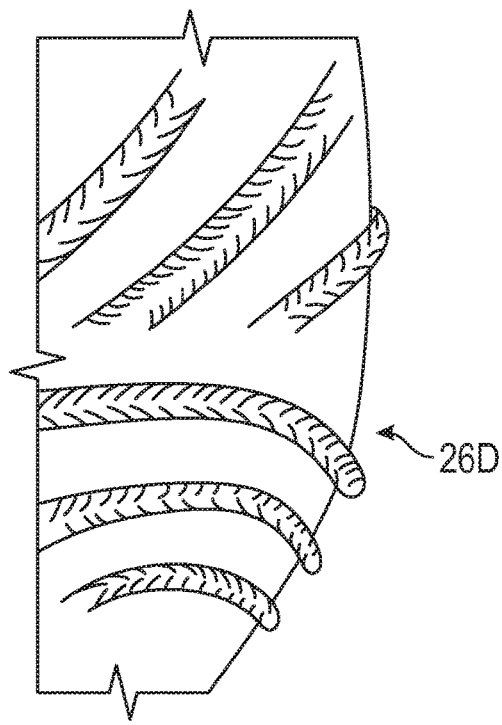
FIG. 4A is an exemplary configuration of a side view of a stimulatory fluid collection device depicting regularly distributed raised ridges on the body of the device.
Figure 4B:
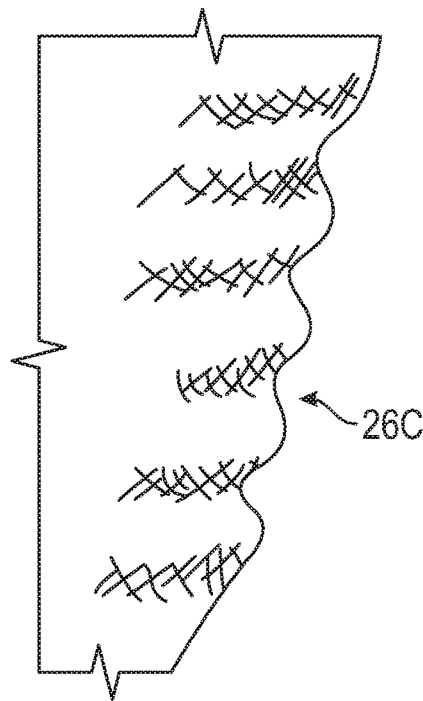
FIG. 4B is an exemplary configuration of a side view of a stimulatory fluid collection device depicting regularly distributed grooves on the body of the device.
Figure 4C:
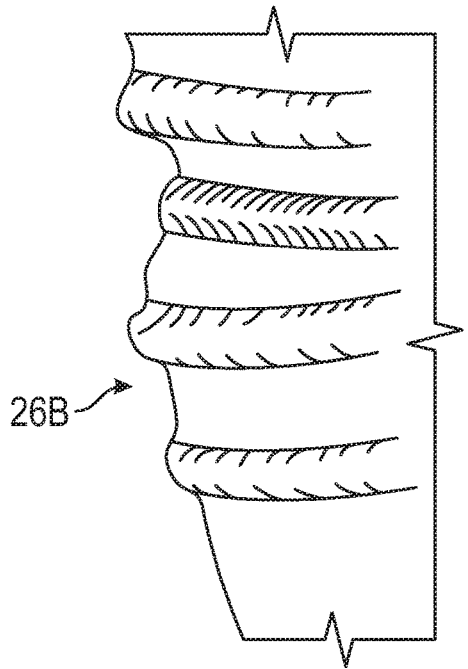
FIG. 4C is an exemplary configuration of a side view of a stimulatory fluid collection device depicting irregularly distributed raised ridges and grooves on the body of the device.
Figure 4D:
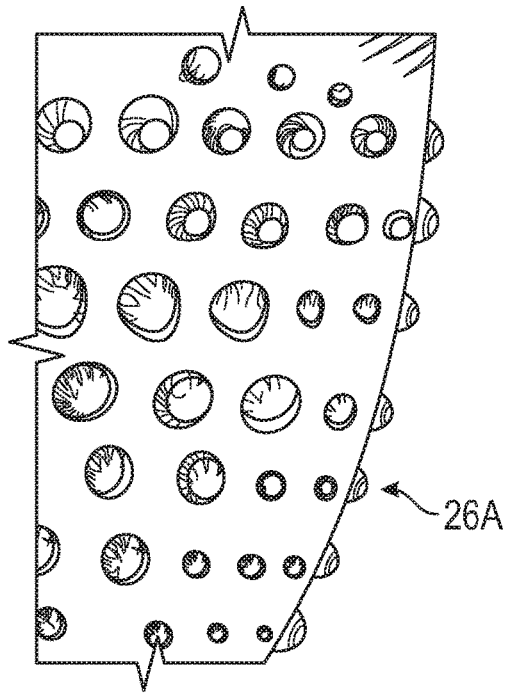
FIG. 4D is an exemplary configuration of a side view of a stimulatory fluid collection device depicting irregularly distributed raised bumps on the body of the device.

In an embodiment depicted in FIG. 4A, texture comprises one or more regularly distributed raised ridges 26D. In another embodiment as depicted in FIG. 4B, texture comprises one or more grooves 26C that are regularly distributed on outer wall surface 18 of stimulating collection device 100. In yet another embodiment depicted in FIG. 4C, texture comprises one or more raised ridges 26B and grooves 26C that are irregularly distributed on outer wall surface 18 of stimulating collection device 100. In another embodiment as depicted in FIG. 4D, texture comprises one or more irregularly distributed raised bumps 26A located on outer wall surface 18 of stimulating collection device 100.

In one exemplary embodiment, raised bumps 26A are about 2 mm to about 15 mm in diameter. In another embodiment, grooves 26C are about 2 mm to about 7 mm wide. In one embodiment, raised ridges 26D are about 2 mm to about 7 mm wide.

In other embodiments, texture comprises one or more grooves, ridges, raised bumps or any combination thereof, covering about 40% to 70% of outer wall surface 18 (not shown). In other embodiments, texture comprises one or more grooves, ridges, raised bumps or any combination thereof, covering about 50% to 90% of outer wall surface 18 (not shown).

In an exemplary embodiment as shown in FIG. 6, stem 22 comprises raised ridges 26D on a single protrusion to provide stimulation to the penis of a user's partner upon contacting outer wall surface 18. Alternatively, texture 26D located on stem 22 provides assistance to the user in removal of device 100. In this embodiment, texture comprises spaced raised ridges 26B and grooves 26C, on outer wall 18 (FIG. 6). In an embodiment, texture is configured to provide stimulation to the penis of the user's partner.

Thus, specific embodiments of a stimulatory fluid collection device and methods to employ such device have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A stimulatory fluid collection device comprising:
    an elongated body comprising a wall having an open top end, a closed bottom end, an inner wall surface defining a collection reservoir configured for collecting and retaining bodily fluid, an outer wall surface, and a plurality of perforations;
    wherein said outer wall surface comprises one or more grooves, raised ridges, raised bumps or a combination thereof;
    wherein said top end of said wall comprises an upper rim section;
    wherein said bottom end of said wall comprises a plurality of stems; and
    wherein said plurality of stems are configured to stimulate a penis of a user's partner.

2. The stimulatory fluid collection device according to claim 1, wherein said body comprises a conical shape.

3. The stimulatory fluid collection device according to claim 1, further comprising an elastomeric material.

4. The stimulatory fluid collection device according to claim 3, wherein said elastomeric material is silicone rubber.

5. The stimulatory fluid collection device according to claim 1, wherein said perforations are evenly spaced and extend from an inner end at said inner wall surface to an outer end at said outer wall surface.

6. The stimulatory fluid collection device according to claim 1, wherein said one or more grooves, raised ridges, raised bumps or a combination thereof are regularly distributed on said outer wall surface.

7. The stimulatory fluid collection device according to claim 1, wherein said one or more grooves, raised ridges, raised bumps or a combination thereof cover about 40% to about 70% of said outer wall surface.

8. The stimulatory fluid collection device according to claim 1, wherein said one or more grooves, raised ridges, raised bumps or a combination thereof are irregularly distributed on said outer wall surface.

9. A conical shaped stimulatory fluid collection device comprising:
- an elongated body comprising a silicone rubber wall having an open top end, a closed bottom end, an inner wall surface defining a collection reservoir configured for collecting and retaining bodily fluid, an outer wall surface, and a plurality of perforations;
- wherein said outer wall surface comprises one or more grooves, raised ridges, raised bumps or a combination thereof;
- wherein said perforations are evenly spaced and extend from an inner end at said inner wall surface to an outer end at said outer wall surface to permit air passage between said inner wall surface and said outer wall surface;
- wherein said top end of said wall comprises an upper rim section;
- wherein said bottom end of said wall comprises a plurality of stems; and
- wherein said plurality of stems are configured to stimulate a penis of a user's partner.

10. The conical shaped stimulatory fluid collection device according to claim 9, wherein said plurality of stems comprise one or more grooves, raised ridges, raised bumps or a combination thereof that are configured to stimulate a penis of a user's partner.

* * * * *